US010542951B2

(12) United States Patent
Klausz et al.

(10) Patent No.: US 10,542,951 B2
(45) Date of Patent: Jan. 28, 2020

(54) SYSTEMS, METHODS, AND DEVICES FOR SIMPLIFIED HIGH QUALITY IMAGING OF BIOPSY SAMPLES ON A MAMMOGRAPHY MACHINE

(71) Applicant: General Electric Company, Schenectady, NY (US)

(72) Inventors: Remy Andre Klausz, Buc (FR); Yann Le Meur, Buc (FR)

(73) Assignee: General Electric Company, Schenectady, NY (US)

(*) Notice: Subject to any disclaimer, the term of this patent is extended or adjusted under 35 U.S.C. 154(b) by 65 days.

(21) Appl. No.: 14/807,769

(22) Filed: Jul. 23, 2015

(65) Prior Publication Data

US 2017/0020473 A1 Jan. 26, 2017

(51) Int. Cl.
*A61B 6/00* (2006.01)
*A61B 6/04* (2006.01)

(52) U.S. Cl.
CPC ............ *A61B 6/502* (2013.01); *A61B 6/04* (2013.01); *A61B 6/0414* (2013.01);
(Continued)

(58) Field of Classification Search
CPC ....... B01L 3/502; A61B 6/502; A61B 6/0414; A61B 6/4411; A61B 6/4494; A61B 6/4417; A61B 6/545; A61B 6/5205; A61B 6/542; A61B 6/04; G01N 2223/309; G01N 2223/6126
See application file for complete search history.

(56) References Cited

U.S. PATENT DOCUMENTS

| 5,383,264 A | 1/1995 | Russell |
| 7,016,460 B2 * | 3/2006 | Saladin ............... A61B 6/0414 |
| | | 378/37 |

(Continued)

FOREIGN PATENT DOCUMENTS

| JP | 2008272093 A | * | 11/2008 |
| JP | 2008272093 A | * | 11/2008 |

OTHER PUBLICATIONS

Machine translation of JP 2008272093.*
(Continued)

*Primary Examiner* — David J Makiya
*Assistant Examiner* — Soorena Kefayati
(74) *Attorney, Agent, or Firm* — Eversheds Sutherland (US) LLP

(57) ABSTRACT

A mammography apparatus including an x-ray source having an x-ray tube with one or more focal spots, a controller for controlling one or more parameters of the x-ray exposure, a digital image receptor configured to generate an x-ray image from objects positioned between the x-ray source and the digital image receptor, a specimen tray configured to receive samples from a biopsy, a positioning arm for positioning the specimen tray between the x-ray source and the digital image receptor, and a detector configured to detect the presence of the specimen tray when it is positioned. The controller is configured to adjust, select or configure one or more parameters of the x-ray exposure in reaction to the detection of the presence of the specimen tray in such a way that the one or more parameters are adapted to the specific needs of imaging biopsy specimens.

12 Claims, 12 Drawing Sheets

(52) U.S. Cl.
CPC ............ *A61B 6/5205* (2013.01); *A61B 6/542* (2013.01); *A61B 6/545* (2013.01)

(56) References Cited

U.S. PATENT DOCUMENTS

| | | | |
|---|---|---|---|
| 7,715,523 B2 | 5/2010 | Lafferty | |
| 8,503,602 B2* | 8/2013 | Lafferty | A61B 10/0096 378/37 |
| 9,117,315 B2* | 8/2015 | Tajima | G06T 15/60 |
| 9,409,164 B2* | 8/2016 | Tawfik | B01L 3/502 |
| 9,597,040 B2* | 3/2017 | Hemmendorff | A61B 6/025 |
| 2009/0225935 A1 | 9/2009 | Eliasson | |
| 2009/0268864 A1* | 10/2009 | Nishida | A61B 6/463 378/37 |
| 2010/0080346 A1 | 4/2010 | Kalender et al. | |
| 2010/0191145 A1 | 7/2010 | Lafferty | |
| 2011/0021947 A1* | 1/2011 | Nakayama | A61B 6/0414 600/567 |
| 2014/0294142 A1* | 10/2014 | Choi | A61B 6/502 378/37 |
| 2016/0007944 A1* | 1/2016 | O'Connor | A61B 6/037 600/431 |
| 2016/0183887 A1* | 6/2016 | Toba | A61B 6/025 600/424 |
| 2016/0183896 A1* | 6/2016 | Muller | A61B 6/481 600/424 |

OTHER PUBLICATIONS

English Machine translation of JP 2008272093A.*
English translation of JP 2008272093.*
English translation of JP 2008272093 (Year: 2008).*
European Search Report and Opinion issued in connection with corresponding EP Application No. 16179743.6 dated Dec. 6, 2016.

* cited by examiner

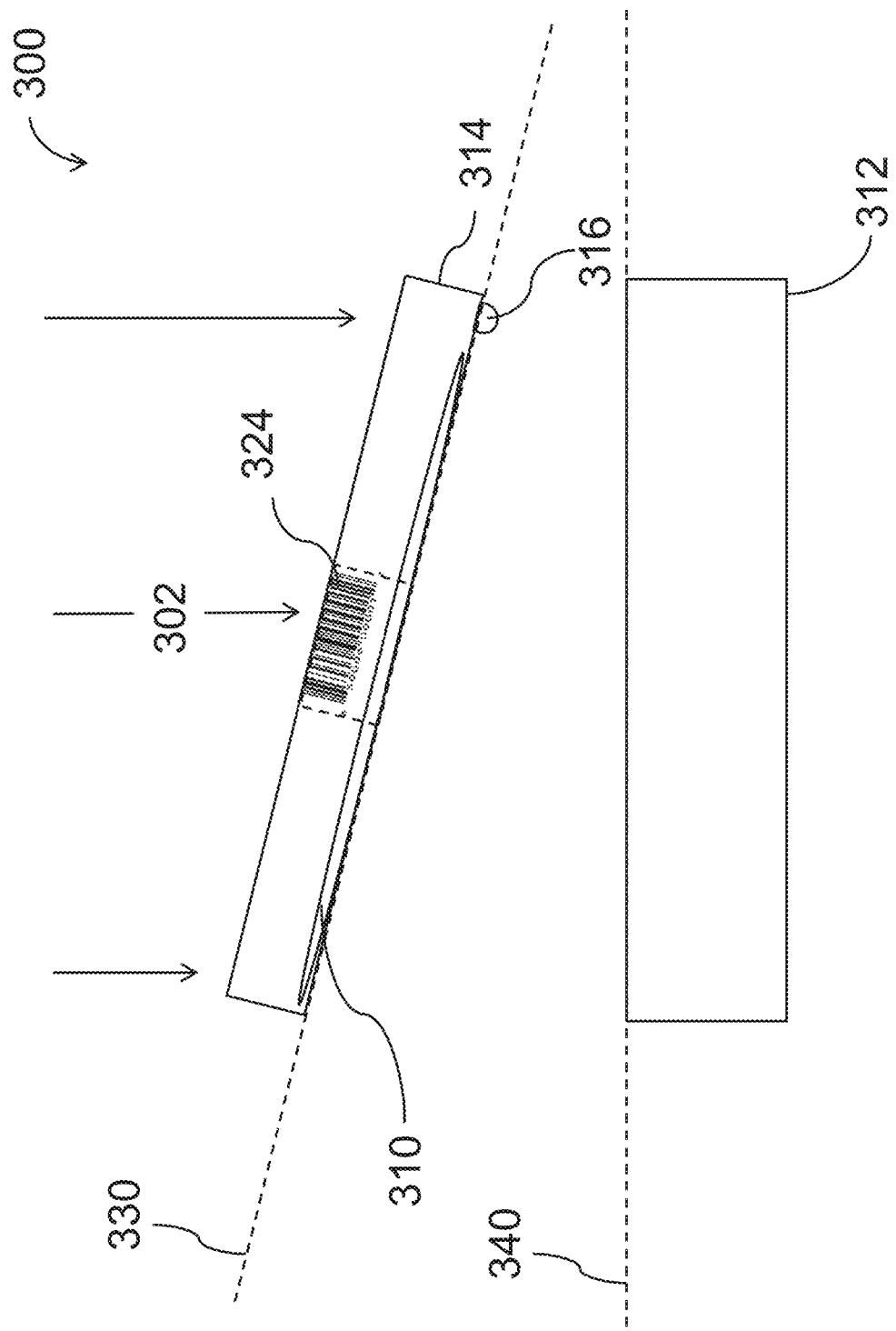

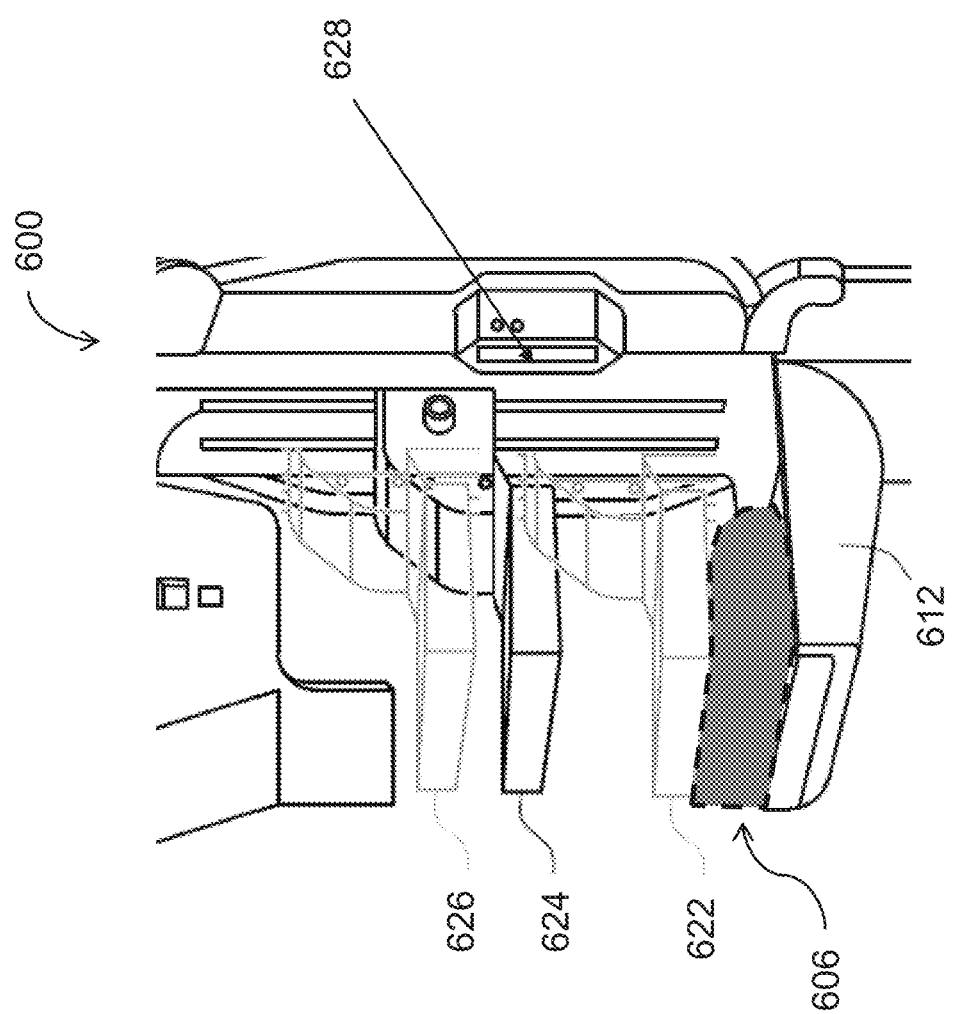

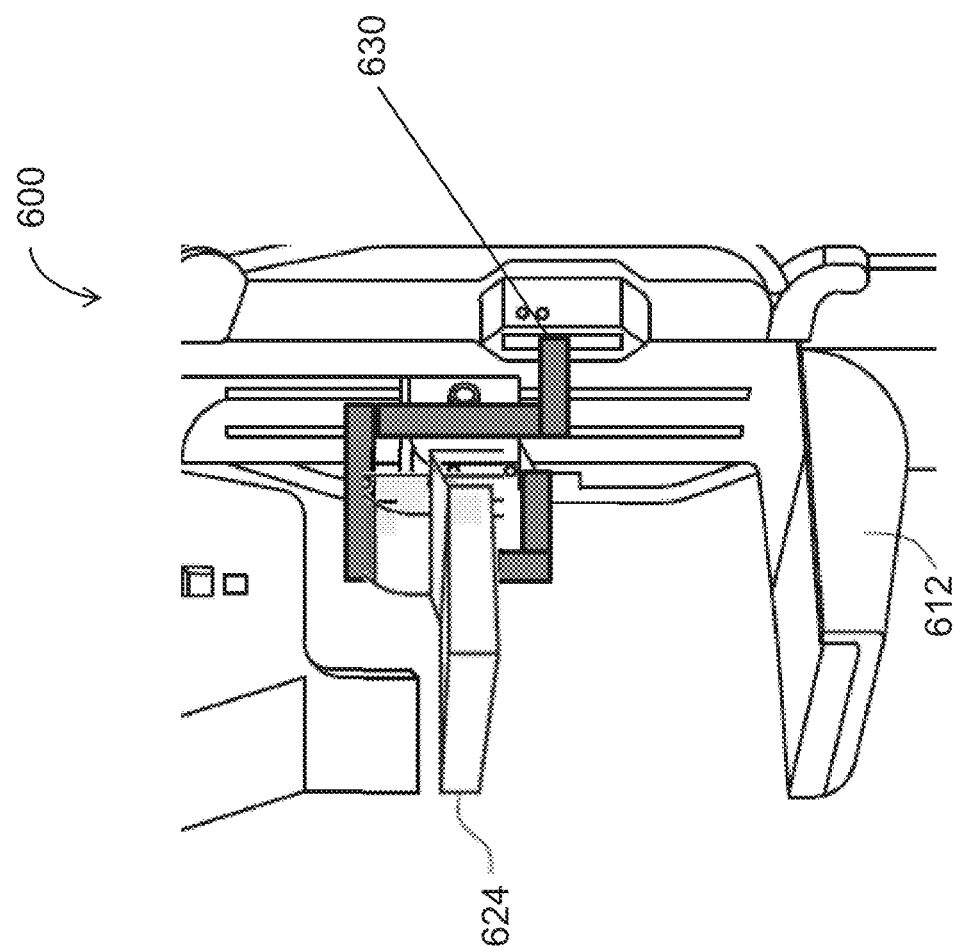

SYSTEMS, METHODS, AND DEVICES FOR SIMPLIFIED HIGH QUALITY IMAGING OF BIOPSY SAMPLES ON A MAMMOGRAPHY MACHINE

TECHNICAL FIELD

Embodiments described herein generally relate to systems, methods and devices for radiological imaging, and more particularly to systems, methods and devices for simplified high quality imaging of biopsy samples on a mammography machine.

BACKGROUND

Stereotactic breast biopsy has become the method of choice for non-surgical diagnosis of many forms of breast cancer. Many breast cancers are discovered by the presence of microcalcifications visible on a screening mammogram. Yet these microcalcifications do not have a corresponding palpable abnormality. Therefore, an image-guided needle biopsy technique must be utilized to determine if early, pre-invasive breast cancer is present. Currently, stereotactically guided needle biopsy procedures represent the state-of-the-art for the common situation outlined above.

However, though very safe and minimally invasive, stereotactic breast biopsy can be laborious, time-consuming and uncomfortable for the patient. In order to immobilize the breast, physical compression must be applied to the breast during the procedure, and the patient must remain motionless. Procedure times are typically between 30-45 minutes, despite recent advances in vacuum-assisted biopsy needle technology. A significant component of procedure time continues to be consumed by the production of specimen radiographs.

A specimen radiograph is an ex-vivo x-ray picture of the biopsy samples or specimen "threads" retrieved from the breast. Under conventional circumstances, this radiograph must be performed on a dedicated x-ray unit 100, such as that shown in FIG. 1, for example. An example of such dedicated x-ray unit is the PathVision™ unit sold by Faxitron Bioptics LLC in Tucson, Ariz. The x-ray picture taken on this unit is required to assure that sufficient quantities of microcalcifications are removed from the groups of visible within the breast. This process proves that the biopsy procedure will be adequate for subsequent analysis by pathology. The process of performing specimen radiography is standard-of-care for stereotactic breast biopsy. However, the x-ray units currently available in the market are very expensive. An alternative method is to use a regular mammography machine in another room, and perform examinations between two patients or two images of a patient. However, users do not have sufficient time or do not take the time necessary to acquire the images under optimal conditions, for example, reconfiguring the mammography machine in geometric magnification mode. As a result, images of poor quality are produced, and the only way to improve the clarity of the images would be to invest heavily on a dedicated x-ray unit as described above.

SUMMARY

Example embodiments described in this disclosure relate to systems, methods, and devices for generating high quality images of biopsy samples on a mammography machine.

One example embodiment is a mammography apparatus including an x-ray source having an x-ray tube with one or more focal spots. The mammography apparatus may also include a controller for controlling one or more parameters of the x-ray exposure. The mammography apparatus may also include a digital image receptor associated with the x-ray source and configured to generate an x-ray image from objects positioned between the x-ray source and the digital image receptor. The mammography apparatus may also include a mobile carriage configured to receive, in normal use, a compression paddle intended to compress the breast of a patient being examined, wherein the paddles may be interchangeable through a rapid fixation system. The mammography apparatus may also include a specimen tray capable to receive samples from a biopsy, and a positioning arm to position the specimen tray between the x-ray source and the digital image receptor. The mammography apparatus may also include a detector for detecting the presence of the specimen tray when it is positioned. The controller is configured to adjust, select or configure one or more parameters of the x-ray exposure in reaction to the detection of the presence of the specimen tray in such a way that the one or more parameters are adapted to the specific needs of imaging biopsy specimens.

According to one or more example embodiments, the specimen tray can be attached to the mobile carriage receiving the compression paddle. In one or more example embodiments, the specimen tray may be attached to the mobile carriage in place of a compression paddle. According to one or more example embodiments, the one or more parameters may include at least one of a focal spot of the x-ray tube, an x-ray field of the x-ray source, a position of the specimen tray, an anode material of the x-ray tube, x-ray beam filtration, x-ray tube voltage, and a current time product (mAs) applied to the x-ray source. In one or more example embodiments, the specimen tray may include a base plate essentially parallel to the digital image receptor when attached to the apparatus. In one or more example embodiments, the specimen tray may be made of a radiolucent material. According to one or more example embodiments, the specimen tray may be configured to receive biopsy samples contained in the receptacles of a vacuum assisted biopsy device. In one or more example embodiment, the specimen tray may include a base and a plurality of sections separated by one or more walls. Each of the plurality of sections may be marked by a radiopaque identifier to identify the breast biopsy samples placed in the respective sections. According to one or more example embodiments, the specimen tray may include one or more grooves to receive a fluid from the one or more breast biopsy samples. In one or more example embodiments, the base plate may be angulated relative to the digital image receptor when attached to the apparatus to enable movement of a fluid from the one or more breast biopsy samples, and the grooves may be angulated relative to the base plate angulation. According to one or more example embodiments, the specimen tray may include an identifier for identification of a patient from whom the one or more breast biopsy samples have been extracted. The identifier may include at least one of a barcode, a radio frequency ID, a near field communication ID, and a quick response code.

One example embodiment is a radiological imaging system including an x-ray source comprising an x-ray tube with one or more focal spots. The system may also include a controller for controlling one or more parameters of the x-ray exposure. The system may also include a receptor configured to generate an x-ray image of an object positioned between the x-ray source and the receptor. The system may also include a specimen tray configured to receive one or more samples from a biopsy. The system may also include a positioning arm for positioning the specimen tray between the x-ray source and the receptor. The system may also include a detector for detecting the presence of the specimen tray when it is positioned. The controller is configured to adjust, select or configure one or more parameters of the x-ray exposure in reaction to the detection of the presence of the specimen tray in such a way that the one or more parameters are adapted to the specific needs of imaging biopsy specimens.

According to one example embodiment, the receptor may include a digital image receptor. According to one example embodiment, the positioning arm may be coupled to a mobile carriage configured to receive a compression paddle. According to one example embodiment, the detector may include a relay sensor, which may be mechanical, optical or magnetic in nature. In one example embodiment, the specimen tray may be attached to the mobile carriage receiving the compression paddle. In one or more example embodiments, the specimen tray may be attached to the mobile carriage in place of a compression paddle. According to one or more example embodiments, the one or more parameters may include at least one of a focal spot of the x-ray tube, an x-ray field of the x-ray source, a position of the specimen tray, an anode material of the x-ray tube, x-ray beam filtration, x-ray tube voltage, and a current time product (mAs) applied to the x-ray source. In one or more example embodiments, the specimen tray may include a base plate essentially parallel to the digital image receptor when attached to the apparatus. In one or more example embodiments, the specimen tray may be made of a radiolucent material. According to one or more example embodiments, the specimen tray may be configured to receive biopsy samples contained in the receptacles of a vacuum assisted biopsy device. In one or more example embodiment, the specimen tray may include a base and a plurality of sections separated by one or more walls. Each of the plurality of sections may be marked by a radiopaque identifier to identify the breast biopsy samples placed in the respective sections. According to one or more example embodiments, the specimen tray may include one or more grooves to receive a fluid from the one or more breast biopsy samples. In one or more example embodiments, the base plate may be angulated relative to the digital image receptor when attached to the apparatus to enable movement of a fluid from the one or more breast biopsy samples, and the grooves may be angulated relative to the base plate angulation. According to one or more example embodiments, the specimen tray may include an identifier for identification of a patient from whom the one or more breast biopsy samples have been extracted. The identifier may include at least one of a barcode, a radio frequency ID, a near field communication ID, and a quick response code.

One example embodiment is a method for imaging breast biopsy samples. The method may include attaching a specimen tray comprising one or more biopsy samples to a mobile carriage on a mammography unit, detecting, by a detector, the presence of the specimen tray, and determining, by a controller, one or more parameters of the x-ray exposure in reaction to the detection of the presence of the specimen tray in such a way that the one or more parameters are adapted to the specific needs of imaging biopsy specimens. According to one example embodiment, the one or more parameters may include at least one of a focal spot of an x-ray tube, an x-ray field, a position of the specimen tray, an anode material of an x-ray tube, x-ray beam filtration, x-ray tube voltage, and a current time product (mAs) applied to an x-ray source.

Example embodiments disclosed avoid the purchase of a dedicated biopsy sample camera, and provide a safe and fast use of a regular mammographic machine for optimal imaging of biopsy samples. The system is simple to set up and provides a low cost implementation for existing machines. These and other advantages may be provided by exemplary embodiments described in more detail below.

BRIEF DESCRIPTION OF THE DRAWINGS

FIG. 3C is a schematic view of a specimen tray and a support table on a mammography apparatus, according to one or more example embodiments of the present disclosure;

FIG. 7B is a close-up view of the mammography apparatus in FIG. 6, according to one or more example embodiments of the present disclosure; and FIG. 7C is a close-up view of the mammography apparatus in FIG. 6, according to one or more example embodiments of the present disclosure.

The following description and the drawings sufficiently illustrate specific embodiments to enable those skilled in the art to practice them. Other embodiments may incorporate structural, process, and other changes. Portions and features of some embodiments may be included in, or substituted for, those of other embodiments. Details of one or more implementations are set forth in the accompanying drawings and in the description below. Further embodiments, features, and aspects will become apparent from the description, the drawings, and the claims. Embodiments set forth in the claims encompass all available equivalents of those claims.

DETAILED DESCRIPTION

Example embodiments described in this disclosure relate to systems, methods, and devices for generating high quality images of biopsy samples in mammography.

Figure 1:
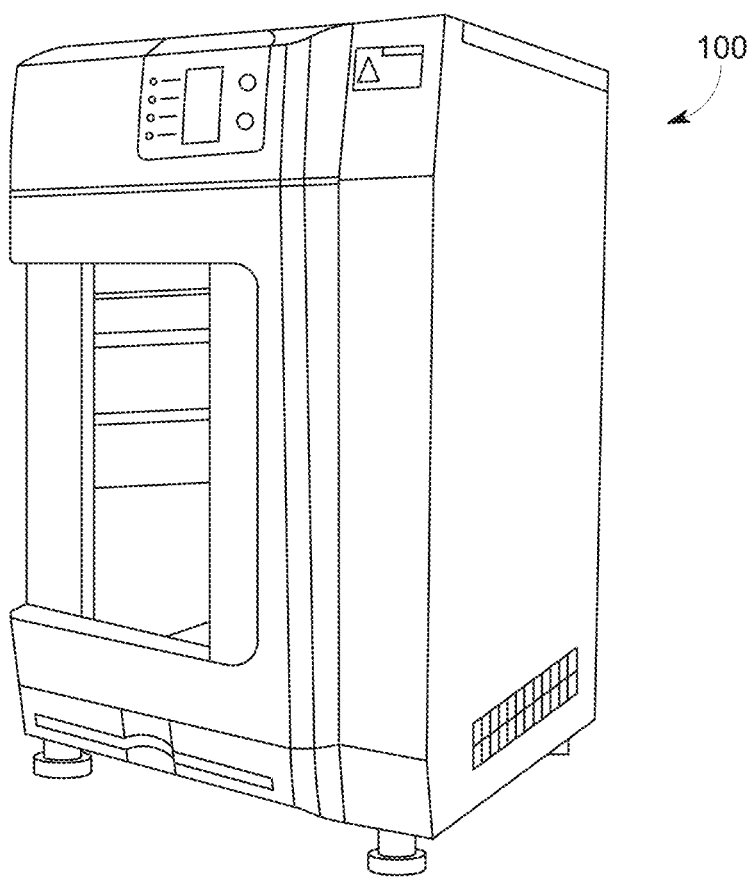
FIG. 1 depicts an illustrative schematic diagram of a conventional specimen radiography system, according to the teachings of the prior art.
Figure 2A:
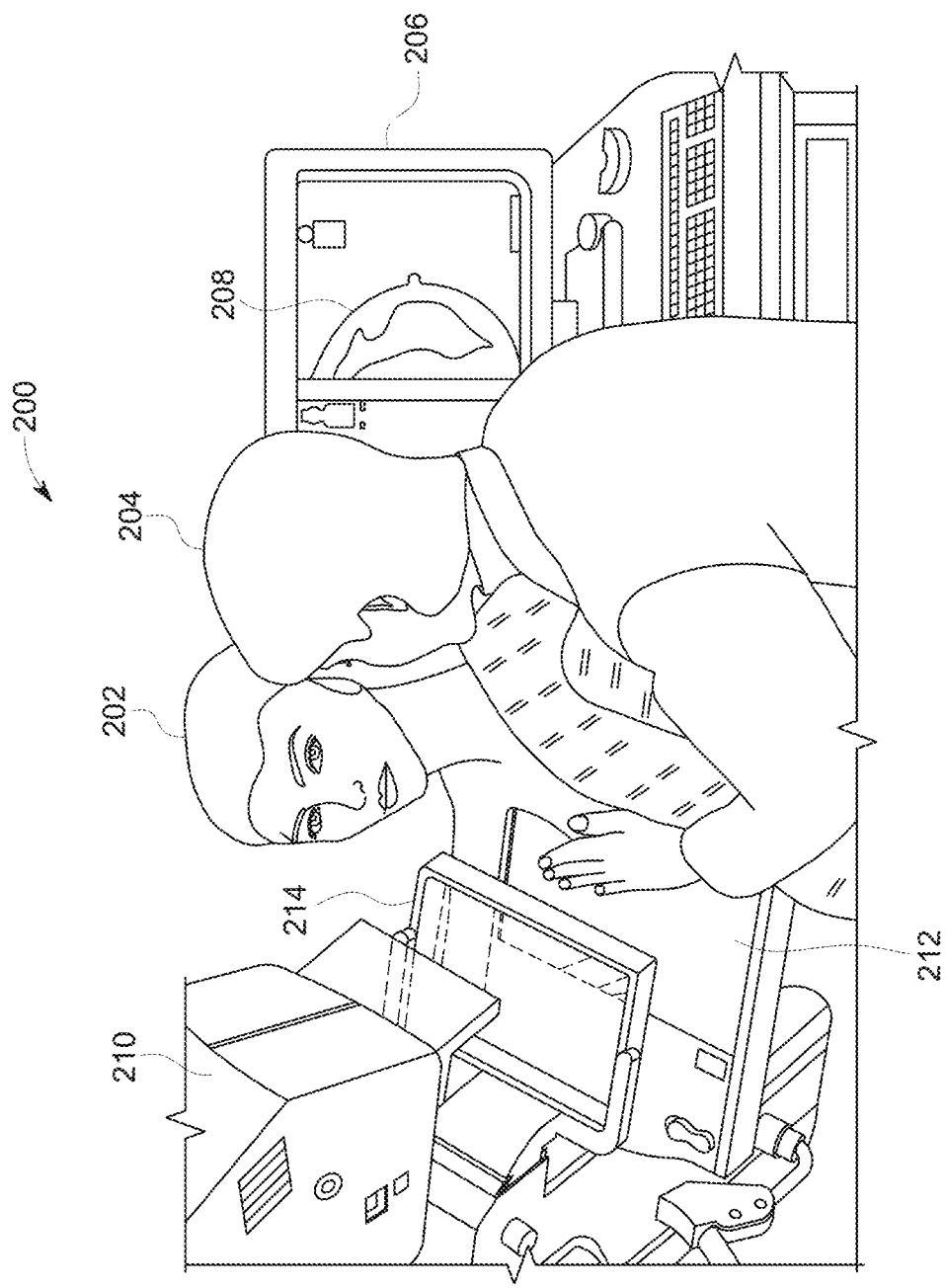
FIG. 2A depicts an illustrative schematic diagram of a mammography system, according to one or more example embodiments of the present disclosure.

FIG. 2A illustrates an example radiological imaging system or mammography system 200, according to one or more example embodiments of the present disclosure. System 200 may include a breast support table 212, which is used to support a breast of a patient 202. Under normal operation, a physician or a radiology technologist 204 may use the breast support table 212 to position the patient's breast such that a complete view of the breast is captured by a digital image receptor included under the breast support table. System 200 generally also includes a compression paddle 214 for compressing the patient's breast against the breast support table. The compression paddle 214 includes a base that is substantially flat, and one or more walls adjoining the base, which is used to restrict a certain portion of the breast under test. The compression paddle 214 is mounted on a mobile carriage which can carry the compression paddle in a first direction along the column that supports the breast support table 212. The mobile carriage may include a bracket or any rapid fixation system for easy mounting and dismounting of the compression paddle. The compression paddle 214 may be made of a transparent material. In some embodiments, the entire compression paddle 214 is transparent. The base and one or more walls of the compression paddle 214 can be of any thickness suitable for the purpose. The base or one or more walls of the compression paddle 214 may have one or more holes having a shape such as square, rectangle, circular, semi-circular, oval, octagonal, polygonal, or combinations thereof.

System 200 also includes an x-ray unit 210 including an x-ray source having a controller for transmitting an x-ray beam onto the patient's breast under normal operation. System 200 also includes a digital image receptor associated with the controller. The digital image receptor is included in the support table, and may form part of the support table or in its entirety. In some embodiments, the x-ray unit 210 may include an x-ray tube with an anode material, such as Molybdenum or Rhodium. The controller is configured to select a focal spot of the x-ray tube based on the application. The controller may include a microprocessor or a microcontroller which is operatively coupled with the x-ray unit 210 and is configured to adjust, select, or configure one or more parameters of the x-ray exposure. The patient's breast is positioned to enable an x-ray image 208 of the patient's breast to be formed upon the digital image receptor. X-ray unit 210 may include a single or dual tube track, which may use one or both materials, Molybdenum or Rhodium, or Tungsten as needed.

A size of the field of view or the x-ray field is from approximately about 19.2×23 cm to 24×31 cm in contact mode, and about 13×23 in magnification mode. The system 200 is configured to provide approximately 3× geometric magnification for a flat object and 1.25 to 2 for a breast. The system 200 can operate either in "contact mode" with the imaged object, such as the breast lying on the breast support 212, or in "magnification mode" when the imaged object is raised closer to the focal spot, such as the biopsy samples. For a regular mammographic examination the breast is positioned on a so-called "magnification stand" so that the image of the structures inside the breast are enlarged by homothecy by a factor typically from 1.25 to 2. However, using the specimen tray it becomes possible to raise the specimen closer to the focal spot until the position giving the best spatial resolution, taking into account the properties of the detector (DQE, MTF) and the dimension of the focal spot of the x-ray tube. According to the invention, the specimen tray is directly positioned in this configuration using a single attachment, or the specimen tray is fixed on the compression carriage, and the controller moves the carriage to a position where the plane of the specimens has the optimum resolution as stated above.

System 200 may also include a computing device 206, which is connected to, for example, a picture archiving and communication system (PACS) and is coupled to the controller described above. FIG. 2 illustrates only one particular example of computing device 206, and other examples of computing device 206 is used in other instances. Although shown in FIG. 2A as a stand-alone computing device 206 for purposes of example, a computing device is any component or system that includes one or more processors or other suitable computing environment for executing software instructions.

According to one or more example embodiments, compression paddle 214 is replaced with a specimen tray, which is similar in size and shape to the compression paddle 214 or better fitted to its role of a tray. The specimen tray is configured to receive one or more breast biopsy samples extracted from a patient's breast. System 200 may include a detector for detecting when the compression paddle 214 is replaced with a specimen tray. Example details of the detector are provided in the following example embodiments with reference to FIGS. 2B and 2C.

Figure 2C:
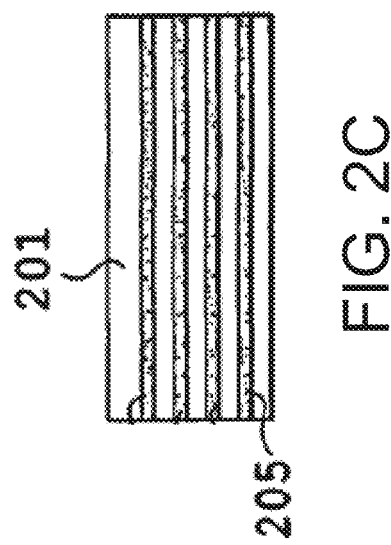
FIG. 2C is a back view of a specimen tray, according to one or more example embodiments of the present disclosure.
Figure 2B:
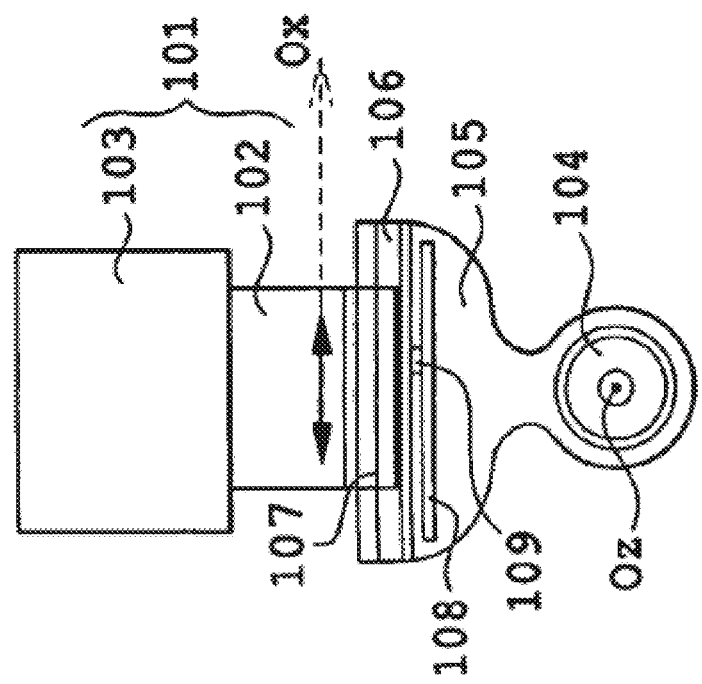
FIG. 2B is a top view of a specimen tray and a mobile carriage, according to one or more example embodiments of the present disclosure.

FIG. 2B illustrates a top view of the system 200 shown in FIG. 2A. In this example embodiment, compression paddle 103 is held by an arm 102 fixed to the carriage which is used to move or shift compression paddle 103 with respect to column 104 of a mammography apparatus, according to one or more example embodiments. Compression paddle 103 may, under normal operation, compress the breast against a breast-support plate 212, such as that shown in FIG. 2A, for example. A breast compressed in this way may then be irradiated optimally, and thus a good image is obtained with minimum radiation. The compression paddle 101 is fixed, through the arm 102, to a mobile carriage 105. Carriage 105 is in addition mobile in translation along an axis Oz. The mobility of the carriage 105 may enable a breast to be compressed between the paddle 101 and the breast-support tray. The carriage 105 is fixed, through a sliding link, to column 104. The motion of the carriage is obtained either through a worm screw, or through a toothed rack or by any other device or equivalents thereof known to one skilled in the art.

Carriage 105 may include a rail 106 in which a bump 107 of the paddle is made to slide, the external dimensions of the bump 107 corresponding to the internal dimensions of the rail 106. This enables the mobile carriage 105 and the compression paddle 101 to be fixedly joined during motions along the axis Oz of the carriage 105. The introduction of the paddle 101 into the carriage 105 is done in a direction Ox perpendicular to the direction Oz. Thus, during compression along the axis Oz, there is no risk that the pad 101 will move along the axis Ox, the compressive force being perpendicular to this axis. However, locking devices, for example, clip-type devices or equivalents thereof, can be used to lock the pad to the carriage once it is in position. Other modes of positioning the pad can be used, for example, modes using hooks.

Carriage 105 may also include a printed circuit 108. A surface of the printed circuit 108 is parallel to a rear face of the compression paddle 101. The term "rear face" of the compression pad 101 shall be understood to mean that face of the compression pad 101 that is in contact with the mobile carriage 105. The rear face of the compression pad fixed to the mobile carriage 105 is before a front face of carriage 105. The printed circuit 108 comprises at least one detector 109, for example a relay sensor, fixed to circuit 108. Circuit 108 is fixed to the carriage 105 in such a way that the detector 109 can read the identifier of identification of the compression paddle 101. The circuit 108 preferably is close to the front face of the carriage 105.

FIG. 2C illustrates a rear face 201 of the compression paddle assembly. The rear face 201 may include parallel tracks, or actuators, 205. These tracks 205 is oriented along the axis Ox defined for FIG. 2B. The nature of the tracks may depend on the nature of the detector 109. If the tracks 109 are mechanical relays, then a track is a lengthwise bump of the rear face 201. By its presence, this bump sets up a contact between the two terminals of the relay. A mechanical track of this kind is, for example, a roller track or a slider track of the cam track type, with at least two levels corresponding to two levels of electrical signals. If it is a magnetic relay, the track is then a magnetized track detectable by magnetic relay. If it is an optical relay, the track is then a thin track made of a reflecting substance. Additional equivalent devices can be made or proposed by one skilled in the art. Each track can be seen as an information bit. For example, if the track is present, the bit is at 1, and if the track is not present, then the bit is at 0. The number of relays for the reading of identification information contained in the circuit 108 determines the dynamics of detection by the mammography apparatus. If circuit 108 has three relays for the detection of identification tracks, then the mammography apparatus has a recognition capacity defined by three bits, that is the mammography apparatus is capable of distinguishing 2^3 rear faces of different compression pads.

In the embodiment of FIG. 2C, rear face 201 potentially comprises four tracks. The presence of a track is detected and corresponds to a value 1, the absence of a track corresponds to non-detection and therefore to a value 0. Thus, with four detectable tracks, namely with four relays for reading position on the circuit 108, it is possible to detect sixteen different states for a rear face, namely sixteen different compression pads. The identification tracks 205 extend along the direction Ox so that they can be detected whatever the position of the compression pad on the mobile carriage. This extension is equal to at least two-thirds of the width of the rear face of the compression pad. Tracks 205 is centered, along the axis Ox, on an axis parallel to the axis Oz and divide the rear face of the pad into two equal parts.

Example embodiments disclosed provide a compression paddle with an identifier for identification. The identifier for identification works together with the detector for reading placed on a mobile carriage that supports the compression paddle. The identifier is passive and may not need any power supply. The identifier is accessible, in read mode, whatever the position of the compression pad on the mobile carriage. To supplement the information accessible on the paddle, it also comprises for enabling the mobile carriage to read the position of the pad in relation to the carriage. Knowledge of this position makes it possible to take account of the specific characteristics of shape of the pad during irradiation. The identifier may include, for example one or more relays, which is mechanical, optical or magnetic. If the relay is mechanical, then the identifier may include tracks extending in a direction along which the pad is mobile so that it can be positioned with respect to the mobile carriage. Through this extension of the identifier, the identification of the paddle can be made independent of this position with respect to the carriage.

Similar to the embodiments illustrated and described with respect to FIGS. 2B and 2C, a specimen tray is detected by a detector, as described in the above example embodiments, when the specimen tray is inserted in place of a compression paddle. The detector is mechanical, magnetic, or optical as described above, or may include additional sensors which is configured to read barcodes, QR codes, RFIDs and the like, which is included on one or more surfaces of the specimen tray. The detector is operatively coupled to the controller of the x-ray unit such that the detector transmits a signal to the controller when it detects the insertion of a specimen tray on the mobile carriage. The controller may include one or more processors which may be configured to implement functionality and/or process instructions for execution within the x-ray unit. For example, processors may be capable of processing instructions stored in a storage device. Examples of processors may include, any one or more of a microprocessor, a controller, a digital signal processor (DSP), an application specific integrated circuit (ASIC), a field-programmable gate array (FPGA), or equivalent discrete or integrated logic circuitry.

The specimen tray is configured to receive one or more biopsy samples from a core needle device, which uses a large hollow needle to remove one sample of breast tissue per insertion, or a vacuum assisted biopsy device which uses a vacuum powered instrument to collect multiple tissue samples during one needle insertion. When the specimen tray replaces the compression paddle on the mammography apparatus, the detector may send a signal to the controller and the controller is configured to adjust, select or configure one or more parameters of the x-ray exposure in reaction to the detection of the presence of the specimen tray in such a way that the one or more parameters are adapted to the specific needs of imaging biopsy specimens. According to one or more example embodiments, the one or more parameters may include at least one of a focal spot of the x-ray tube, an x-ray field of the x-ray source, a position of the specimen tray, an anode material of the x-ray tube, x-ray beam filtration, x-ray tube voltage, and a current time product (mAs) applied to the x-ray source.

Figure 3A:
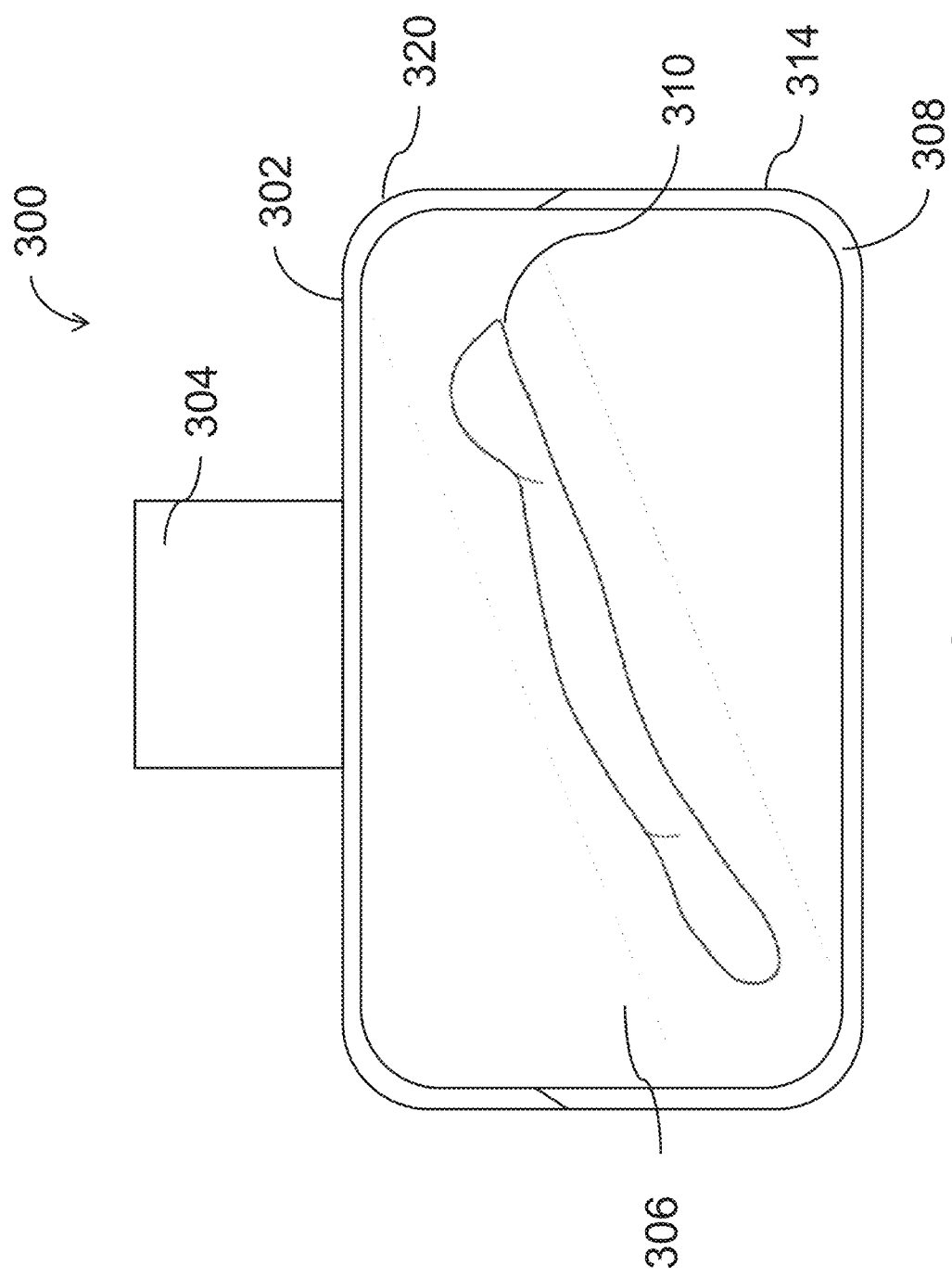
FIG. 3A is a top view of a specimen tray in a mammography apparatus, according to one or more example embodiments of the present disclosure.
Figure 3B:
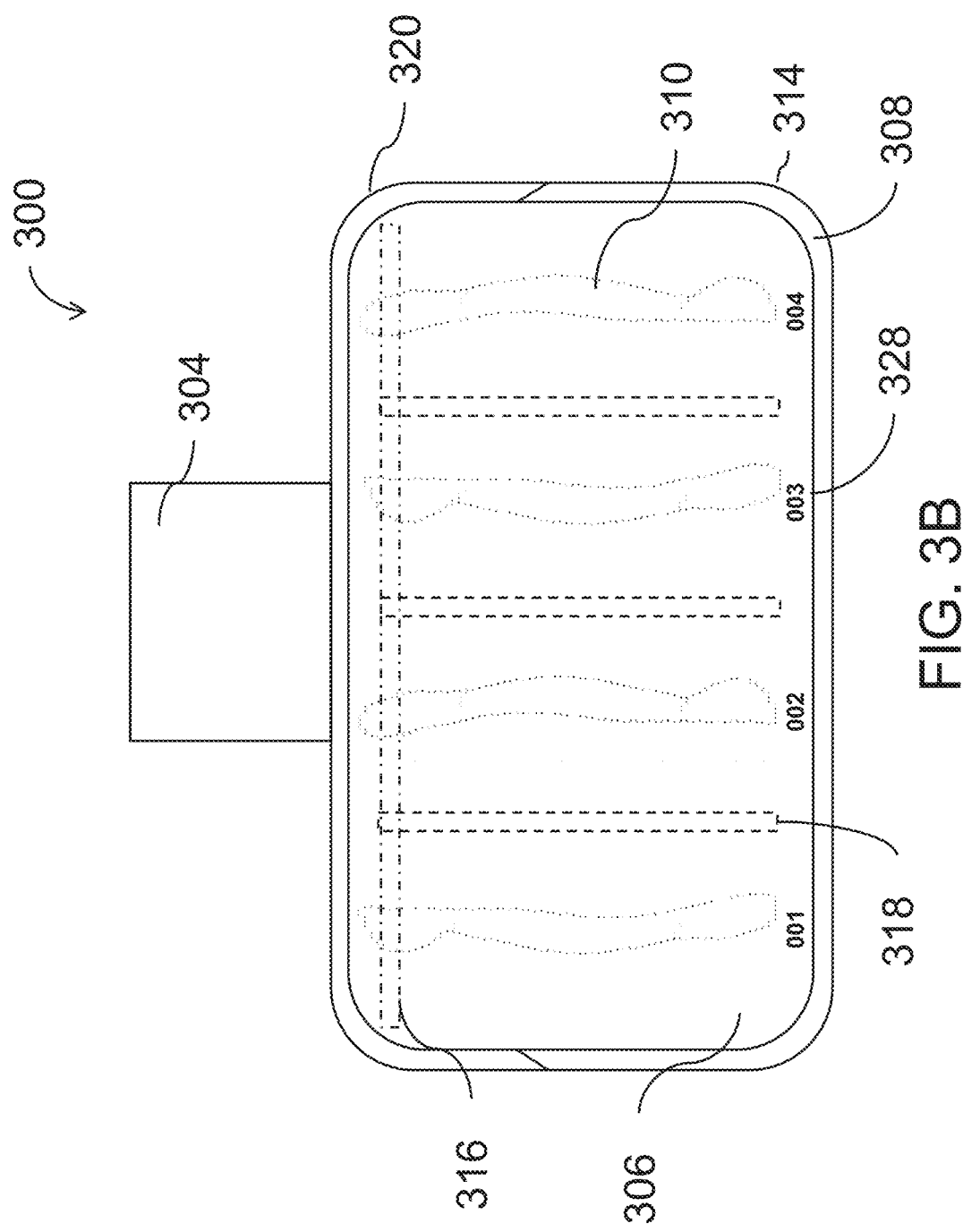
FIG. 3B is a top view of a specimen tray in a mammography apparatus, according to one or more example embodiments of the present disclosure.

FIGS. 3A-3C illustrates one or more configurations 300 of an example specimen tray 308, according to one or more example embodiments of the present disclosure. As illustrated in FIG. 3A, the specimen tray 308 may be attached to the mobile carriage using an arm 304. Arm 304 may include a bracket 320 for receiving the compression paddle under normal operation. Bracket 320 may include one or more grooves so the compression paddle may be easily removed and replaced with the specimen tray 308. In one or more example embodiments, the specimen tray may be attached to the mobile carriage in place of a compression paddle. Surface 302 may include one or more identifiers as described in the above example embodiments. The specimen tray 308 may include a base plate 306 essentially parallel to the digital image receptor when attached to the apparatus, and a wall 314 around at least a portion of the circumference of the specimen tray 308. In one or more example embodiments, the base plate 306 of the specimen tray 308 is made of a radiolucent material such that x-rays may easily pass through the specimen tray. According to one or more example embodiments, the specimen tray 308 may be configured to receive biopsy samples 310 contained in the receptacles of a vacuum assisted biopsy device.

As illustrated in FIG. 3B, the specimen tray 308 may include a base 306 and a plurality of sections separated by one or more walls 318. Each of the plurality of sections may be marked by a radiopaque identifier 328 to identify the breast biopsy samples 310 placed in the respective sections. According to one or more example embodiments, the specimen tray 308 may include one or more grooves 316 to receive a fluid from the one or more breast biopsy samples 310.

As illustrated in FIG. 3C, the base plate 306 of the specimen tray 308 may be at an angle 330 relative to a plane 340 of the digital image receptor 312 when attached to the apparatus to enable movement of a fluid 326 from the one or more breast biopsy samples 310. According to one example embodiment, the grooves 316 may be angulated relative to the base plate angulation 330. According to one or more example embodiments, the specimen tray 308 may include an identifier 324 for identification of a patient from whom the one or more breast biopsy samples 310 have been extracted. The identifier 324 may be removably or irremovably attached to at least one surface or wall of the specimen tray 308 and may include at least one of a barcode, a radio frequency ID, a near field communication ID, and a quick response code.

Figure 4:
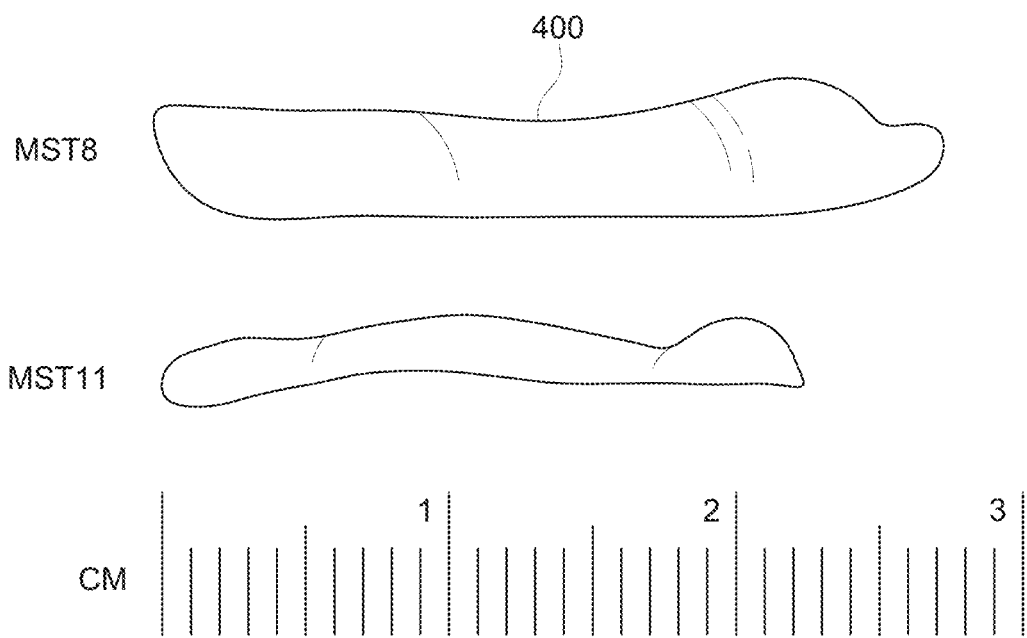
FIG. 4 depicts an illustrative schematic diagram of breast biopsy samples extracted from a patient's breast on a mammography apparatus, according to one or more example embodiments of the present disclosure.

FIG. 4 illustrates a schematic of the breast samples 400 obtained from a patient's breast, as discussed in the above example embodiments. Each of these samples may have a length of approximately about 1-10 cm or more, and may have a thickness of 0.15-5 cm or more. According to one example embodiment, high quality images of the biopsy samples may be captured using regular mammographic equipment. The focal spot of the x-ray tube in x-ray unit 210 may be adjusted or selected to improve the clarity of the x-ray images as desired. The position of the specimen tray may be moved automatically or after validation by an operator to a position corresponding to a geometric magnification factor providing an improved image quality compared to placing the samples on a regular breast support plate for 'contact' operation. Compared to patient images, there is no risk of patient movement or excessive irradiation. So it is possible to use the smallest available focal spot at the same time as a high geometric magnification obtained by selecting a position for the samples providing the best possible spatial resolution and/or modulation transfer function (MTF) of the acquired images. This would in general correspond to a focal spot of 0.1 and a magnification factor between 2 and 3. The same way, a soft radiation adapted to the small thickness of the samples may be selected, such as a molybdenum or tungsten anode filtered with a molybdenum or aluminum filter operated at 20-25 kV. One or more parameters of the system 200, for example, the anode material, beam filtration, and x-ray tube voltage may be automatically set to values adapted to a specific use based at least on the thickness of the biopsy samples. For example, the controller is configured to adjust, select or configure one or more parameters of the x-ray exposure in reaction to the detection of the presence of the specimen tray in such a way that the one or more parameters are adapted to the specific needs of imaging biopsy specimens. According to one or more example embodiments, the one or more parameters may include at least one of a focal spot of the x-ray tube, an x-ray field of the x-ray source, a position of the specimen tray, an anode material of the x-ray tube, x-ray beam filtration, x-ray tube voltage, and a current time product (mAs) applied to the x-ray source. When the desired image(s) have been acquired, the user may remove the specimen tray and the mammographic equipment may preferably automatically return to its previous operating state, for example mammography state. This provides a very fast way to obtain high quality specimen images without slowing down too much an on-going procedure.

In conjunction with the positioning of the specimen tray and to have the best results with the maximum magnification, according to one or more example embodiments of the disclosure, the controller may select the smallest available focal spot, which in normal use is selected by the insertion of the magnification stand or by an action of the operator on the control panel. In a similar way, the controller may select the lowest reachable x-ray energy, for example by selecting a Molybdenum filter and a high voltage of 25 kV or less. The value of the current-time product through the x-ray tube during the exposure need not be very accurate since the specimen thickness is always small. It may be chosen as high as possible to improve image quality, just limited by the constraint that the images of the zones of the tray without a specimen are below the saturation level of the detector. The exposure duration is not critical since the specimen remains stationary during the exposure, and dose is not an issue for a specimen, unlike the organ of a living patient where radiation can generate radiation-induced damage. One or more of these selections may be automated under the action of the controller following the information that the specimen tray is engaged.

Figure 5:
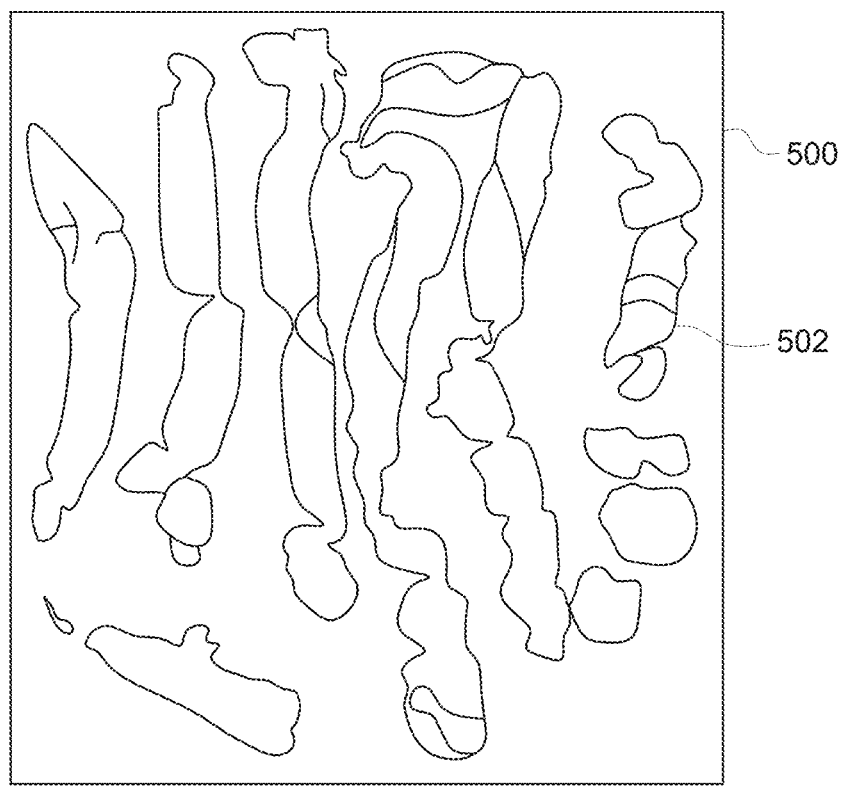
FIG. 5 depicts an illustrative schematic diagram of x-ray images of breast biopsy samples extracted from a patient's breast on a mammography apparatus, according to one or more example embodiments of the present disclosure.

FIG. 5 illustrates a schematic of an x-ray image or radiograph 500 obtained using the one or more methods described in the above example embodiments. Specimen radiograph 500 includes x-ray images of one or more breast biopsy samples 502. According to one or more example embodiments, a mechanism may be provided for allowing the identification of the biopsy sample images acquired with the compression paddle. One advantage of introducing the specimen tray in the mammographic system 200 in place of a regular compression paddle is to enable labeling of the samples as belonging to a specific patient. This can be done using, for example, bar codes, RFIDs, or QR codes which may be removably or irremovably attached to the specimen tray, and may be read by the mammographic system 200. The sample images may be sent to the machine where the patient had the biopsy, or to a picture archiving and communication system (PACS), to be attached to the file of the patient.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments do not include, certain features, elements, and/or steps. Thus, such conditional language is not generally intended to imply that features, elements, and/or steps are in any way required for one or more embodiments.

Figure 6:
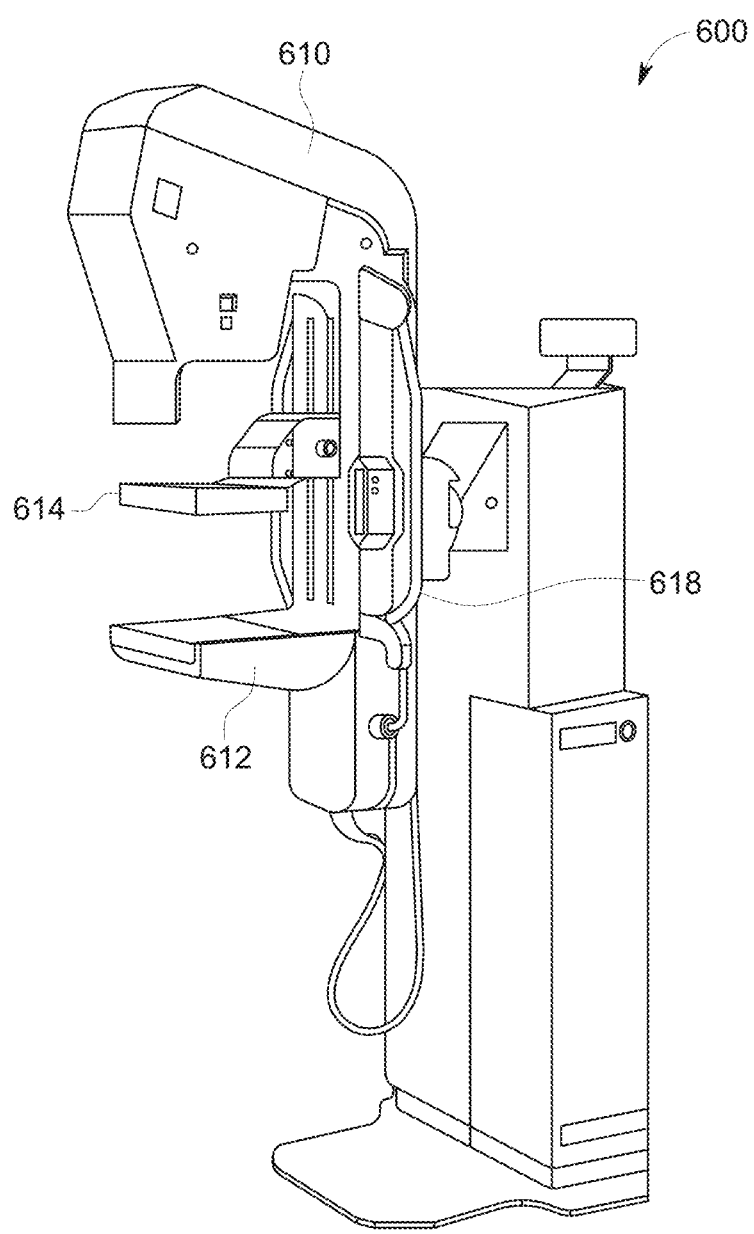
FIG. 6 depicts an illustrative schematic diagram of a mammography apparatus, according to one or more example embodiments of the present disclosure.

FIG. 6 illustrates an example radiological imaging system or mammography system 600, according to one or more example embodiments of the present disclosure. System 600 may include a breast support table 612, which may be used under normal operation to support a breast of a patient. System 600 may also include a compression paddle 614 for compressing the patient's breast against the breast support table. The compression paddle 614 may include a base that may be substantially flat, and one or more walls adjoining the base, which may be used to restrict the breast area to a certain portion of the breast under test. The compression paddle 614 may be mounted on a mobile carriage which can carry the compression paddle in a first direction along the column that supports the breast support table 612. A portion the compression paddle 614 may include a transparent material. In some embodiments, the entire compression paddle 614 may be transparent. The base and one or more walls of the compression paddle 614 may be of any thickness suitable for the purpose. The base or one or more walls of the compression paddle 614 may have one or more holes having a shape such as square, rectangle, circular, semicircular, oval, octagonal, polygonal, or combinations thereof.

System 600 may also include an x-ray unit 610 including an x-ray source having a controller for controlling the exposure and transmitting an x-ray beam onto the patient's breast. System 600 may also include a digital image receptor associated with the controller. The digital image receptor may be included in the support table 612, and may form part of the support table or in its entirety. In some embodiments, the x-ray unit 610 may include an x-ray tube with an anode material, such as Molybdenum or Rhodium. The controller may be configured to select a focal spot of the x-ray tube based on the application. The controller may include a processor which may be operatively coupled with the x-ray unit 610 and is configured to adjust, select, or configure one or more parameters of the x-ray exposure. The x-ray source may be adapted to be positioned to enable an x-ray image of the patient's breast to be formed upon the digital image receptor. X-ray unit 610 may include a dual tube track, which may use one or both materials, Molybdenum or Rhodium, as needed.

A size of the field of view or the x-ray field is from approximately about 19.2×23 cm to 24×31 cm in contact mode, and about 13×23 in magnification mode. The system 600 is configured to provide approximately 3× geometric magnification for a flat object and 1.25 to 2 for a breast. The system 600 can operate either in "contact mode" with the imaged object, such as the breast lying on the breast support 602, or in "magnification mode" when the imaged object is raised closer to the focal spot, such as the biopsy samples. For a regular mammographic examination the breast is positioned on a so-called "magnification stand" so that the image of the structures inside the breast are enlarged by homothecy by a factor typically from 1.25 to 2. However, using the specimen tray it becomes possible to raise the specimen closer to the focal spot until the position giving the best spatial resolution, taking into account the properties of the detector (DQE, MTF) and the dimension of the focal spot of the x-ray tube. According to the invention, the specimen tray is directly positioned in this configuration using a single attachment, or the specimen tray is fixed on the compression carriage, and the controller moves the carriage to a position where the plane of the specimens has the optimum resolution as stated above. System 600 may also include a computing device (not shown), which may be connected to, for example, a picture archiving and communication system (PACS) and may be coupled to the controller described above.

According to one or more example embodiments, compression paddle 614 may be replaced with a specimen tray, which may be similar in size and shape to the compression paddle 614, and may be as described in the illustrative embodiments of FIGS. 3A-3C. The specimen tray may be configured to receive one or more breast biopsy samples extracted from a patient's breast. System 600 may include a detector for detecting when the compression paddle 614 is replaced with a specimen tray. The detector may be mechanical, magnetic, or optical as described in the illustrative examples of FIGS. 2B and 2C, or may include additional sensors which may be configured to read barcodes, QR codes, RFIDs and the like, which may be included on one or more surfaces of the specimen tray. The detector may be operatively coupled to the controller of the x-ray unit such that the detector transmits a signal to the controller when it detects the insertion of a specimen tray on the mobile carriage. The controller may include one or more processors which may be configured to implement functionality and/or process instructions for execution within the x-ray unit. For example, processors may be capable of processing instructions stored in a storage device. Examples of processors may include, any one or more of a microprocessor, a controller, a digital signal processor (DSP), an application specific integrated circuit (ASIC), a field-programmable gate array (FPGA), or equivalent discrete or integrated logic circuitry.

The specimen tray may be configured to receive one or more biopsy samples from a core needle device, which uses a large hollow needle to remove one sample of breast tissue per insertion, or a vacuum assisted biopsy device which uses a vacuum powered instrument to collect multiple tissue samples during one needle insertion. When the specimen tray replaces the compression table on the mammography apparatus, the detector may send a signal to the controller and the controller is configured to adjust, select or configure one or more parameters of the x-ray exposure in reaction to the detection of the presence of the specimen tray in such a way that the one or more parameters are adapted to the specific needs of imaging biopsy specimens. According to one or more example embodiments, the one or more parameters may include at least one of a focal spot of the x-ray tube, an x-ray field of the x-ray source, a position of the specimen tray, an anode material of the x-ray tube, x-ray beam filtration, x-ray tube voltage, and a current time product (mAs) applied to the x-ray source.

According to this example embodiment, high quality images of the biopsy samples may be captured using a dedicated sample-imaging camera housed within the system or using regular mammographic equipment. The images may be captured either in a regular mode or a magnified-image capture mode. The focal spot of the x-ray tube in x-ray unit 610 may be adjusted to improve the clarity of the x-ray images as desired. The position of the specimen tray may be moved automatically or after validation by an operator to a position corresponding to a geometric magnification factor providing an improved image quality compared to placing the samples on a regular breast support plate for 'contact' operation. Compared to patient images, there is no risk of patient movement or excessive irradiation. So it is possible to use the smallest available focal spot at the same time as a high geometric magnification obtained by selecting a position for the samples providing the best possible spatial resolution and/or modulation transfer function (MTF) of the acquired images. This would in general correspond to a focal spot of 0.1 and a magnification factor between 2 and 3. The same way, a soft radiation adapted to the small thickness of the samples may be selected, such as a molybdenum or tungsten anode filtered with a molybdenum or aluminum filter operated at 20-25 kV. One or more parameters of the system 600, for example, the anode material, beam filtration, and x-ray tube voltage may be automatically set to values adapted to a specific use based at least on the thickness of the biopsy samples. For example, the controller is configured to adjust, select or configure one or more parameters of the x-ray exposure in reaction to the detection of the presence of the specimen tray in such a way that the one or more parameters are adapted to the specific needs of imaging biopsy specimens. According to one or more example embodiments, the one or more parameters may include at least one of a focal spot of the x-ray tube, an x-ray field of the x-ray source, a position of the specimen tray, an anode material of the x-ray tube, x-ray beam filtration, x-ray tube voltage, and a current time product (mAs) applied to the x-ray source. When the desired image(s) have been acquired, the user may remove the specimen tray and the mammographic equipment may automatically return to its previous operating state, for example mammography state.

In conjunction with the positioning of the specimen tray and to have the best results with the maximum magnification, according to one or more example embodiments of the disclosure, the controller may select the smallest available focal spot, which in normal use is selected by the insertion of the magnification stand or by an action of the operator on the control panel. In a similar way, the controller may select the lowest reachable x-ray energy, for example by selecting a Molybdenum filter and a high voltage of 25 kV or less. The value of the current-time product through the x-ray tube during the exposure need not be very accurate since the specimen thickness is always small. It may be chosen as high as possible to improve image quality, just limited by the constraint that the images of the zones of the tray without a specimen are below the saturation level of the detector. The exposure duration is not critical since the specimen remains stationary during the exposure, and dose is not an issue for a specimen, unlike the organ of a living patient where radiation can generate radiation-induced damage. One or more of these selections may be automated under the action of the controller following the information that the specimen tray is engaged.

Figure 7A:
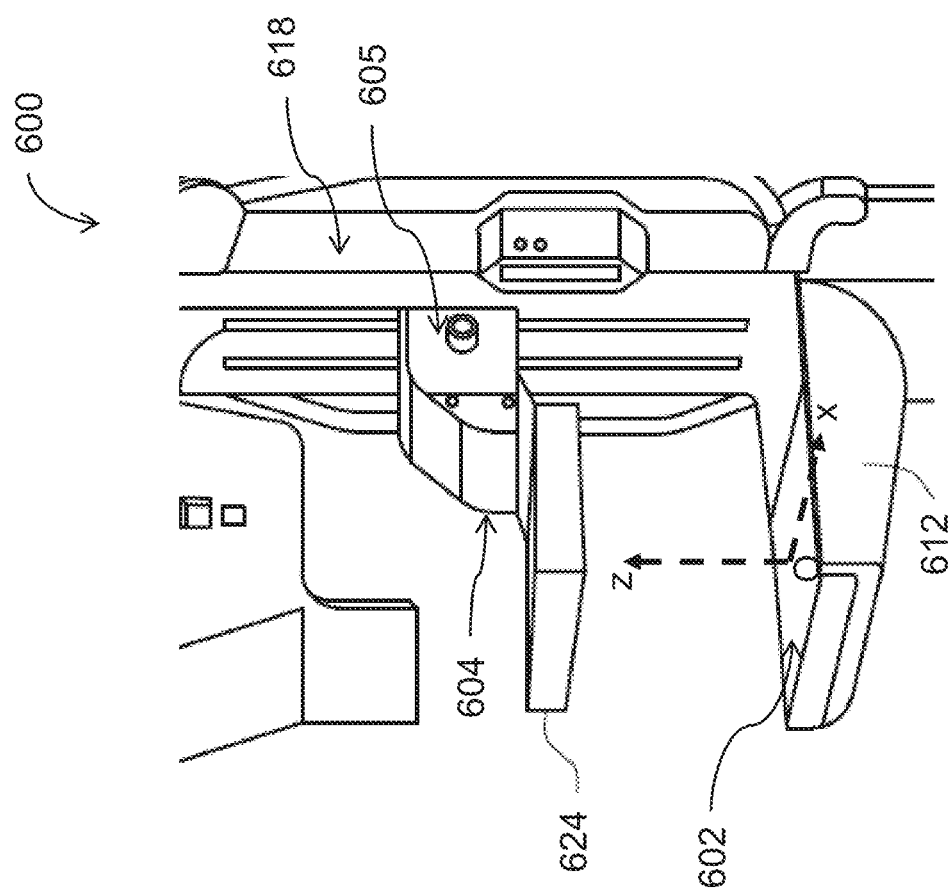
FIG. 7A is a close-up view of the mammography apparatus in FIG. 6, according to one or more example embodiments of the present disclosure.

FIG. 7A illustrates a close-up view of the system 600 described with reference to FIG. 6. In this example embodiment, system 600 includes a mobile carriage 605, which traverses along the length of the main column 618 of the system 600. Mobile carriage 605 includes an arm 604 that supports or is configured to hold the specimen tray 624. System 600 also includes a breast support table 612 on which is a breast support plate 602. According to one example embodiment, the breast support table 612 of system 600 may be moved in the X and Z directions. FIG. 7B illustrates various positions of the specimen tray 624 under operation. Under normal operation compression paddle 622 may compress a patient's breast 606 against the breast support table 612. However, when the specimen tray 624 is being used to image biopsy samples, the mobile carriage 605 may traverse and move the specimen tray 624 closer to the x-ray source and to a new position 626. The extent to which the mobile carriage 605 moves may be determined by the controller, according to one or more example embodiments described above. System 600 also includes a carrying stand 628, which may carry one or more replaceable specimen trays 624 for the sake of user convenience and ready use.

FIG. 7C illustrates an alternative embodiment where the specimen tray 624 may be mounted on a separate or permanent fixture 630 instead of being mounted on the mobile carriage 605. This fixture 630 may be used as a permanent place for mounting the specimen tray 624 when the system 600 is being used for biopsy samples examination. Fixture 630 may be designed in a manner such that the motion of the mobile carriage 605 is not interrupted.

Example embodiments disclosed avoid the purchase of a dedicated sample camera or dedicated x-ray unit, and provide a safe and fast use of a regular mammographic machine for optimal imaging of biopsy samples. The system is simple to set up and provides a low cost implementation for existing machines.

While there have been shown, described and pointed out, fundamental novel features of the disclosure as applied to the example embodiments, it will be understood that various omissions and substitutions and changes in the form and details of examples illustrated, and in their operation, may be made by those skilled in the art without departing from the spirit of the disclosure. Moreover, it is expressly intended that all combinations of those elements and/or method operations, which perform substantially the same function in substantially the same way to achieve the same results, are within the scope of the disclosure. Moreover, it should be recognized that structures and/or elements and/or method operations shown and/or described in connection with any disclosed form or embodiment of the disclosure may be incorporated in any other disclosed or described or suggested form or embodiment as a general matter of design choice. It is the intention, therefore, to be limited only as indicated by the scope of the claims.

The above description with reference to the accompanying drawings is provided to assist in a comprehensive understanding of certain embodiments of the present disclosure as defined by the claims and their equivalents. It includes various specific details to assist in that understanding but these are to be regarded as merely exemplary. Accordingly, those of ordinary skill in the art will recognize that various changes and modifications of the embodiments may be made without departing from the scope and spirit of the present disclosure. In addition, descriptions of well-known functions and constructions may be omitted for clarity and conciseness.

The terms used in the above description and following claims are not limited to their dictionary meanings, but, are merely used to enable a clear and consistent understanding of the present disclosure. Accordingly, it should be apparent to those skilled in the art that the description of embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces. The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

What is claimed is:

1. A mammography apparatus, comprising:
    an x-ray source comprising an x-ray tube with one or more focal spots;
    a controller configured to control one or more parameters of the x-ray exposure;
    a digital image receptor associated with the x-ray source and configured to generate an x-ray image of an object positioned between the x-ray source and the digital image receptor;
    a mobile carriage configured to receive, in normal use, a compression paddle intended to compress a breast of a patient being examined;
    a specimen tray configured to receive one or more samples from a biopsy and to be positioned on the mobile carriage;
    a positioning arm attached to the mobile carriage, the positioning arm configured to position the specimen tray between the x-ray source and the digital image receptor and to translate the specimen tray relative to the x-ray source; and a detector configured to detect the presence of the specimen tray when the specimen tray is positioned on the mobile carriage;

wherein the controller is further configured to adjust, select or configure one or more parameters of the x-ray exposure in reaction to the detection of the presence of the specimen tray on the mobile carriage in such a way that the one or more parameters are adapted to the specific needs of imaging biopsy specimens; and wherein the specimen tray is removably attached to the mobile carriage in place of the compression paddle.

2. The mammography apparatus according to claim 1, wherein the specimen tray is removably attached to the mobile carriage via the positioning arm.

3. The mammography apparatus according to claim 1, wherein the one or more parameters comprise at least one of a focal spot of the x-ray tube, an x-ray field of the x-ray source, a position of the specimen tray, an anode material of the x-ray tube, x-ray beam filtration, x-ray tube voltage, a current time product (mAs) applied to the x-ray source, and display conditions of the acquired image.

4. The mammography apparatus of claim 1, wherein the specimen tray comprises a base plate extending essentially parallel to the digital image receptor when the specimen tray is positioned on the mobile carriage.

5. The mammography apparatus of claim 1, wherein the specimen tray is configured to receive the one or more samples from one or more receptacles of a vacuum assisted biopsy device.

6. The mammography apparatus of claim 1, wherein the specimen tray is made of a radiolucent material.

7. The mammography apparatus of claim 1, wherein the specimen tray comprises a base plate and a plurality of sections separated by one or more walls.

8. The mammography apparatus of claim 1, wherein the specimen tray comprises an identifier for identification of a patient from whom the one or more samples are extracted.

9. The mammography apparatus of claim 7, wherein each of the plurality of sections is marked by a radiopaque identifier to identify respective samples placed in the respective sections.

10. The mammography apparatus of claim 7, wherein the specimen tray comprises one or more grooves to receive a fluid from the one or more samples.

11. The mammography apparatus of claim 7, wherein the base plate is angulated relative to the digital image receptor when the specimen tray is positioned on the mobile carriage to enable movement of a fluid from the one or more samples, and wherein the grooves are angulated relative to the base plate angulation.

12. The mammography apparatus of claim 8, wherein the identifier comprises at least one of a barcode, a radio frequency ID, a near field communication ID, and a quick response code.

* * * * *